United States Patent
Kudo et al.

(10) Patent No.: US 8,625,736 B2
(45) Date of Patent: Jan. 7, 2014

(54) X-RAY CT APPARATUS

(75) Inventors: Yoji Kudo, Otawara (JP); Hiroaki Miyazaki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 176 days.

(21) Appl. No.: 12/755,741

(22) Filed: Apr. 7, 2010

(65) Prior Publication Data

US 2010/0260313 A1 Oct. 14, 2010

(30) Foreign Application Priority Data

Apr. 9, 2009 (JP) ................. P2009-094603
Apr. 5, 2010 (JP) ................. P2010-087227

(51) Int. Cl.
*H05G 1/60* (2006.01)

(52) U.S. Cl.
USPC ............................... 378/19; 378/4

(58) Field of Classification Search
USPC ...................................... 378/19, 4
See application file for complete search history.

(56) References Cited

U.S. PATENT DOCUMENTS

| 6,445,764 | B2 * | 9/2002 | Gohno et al. ............... 378/19 |
| 7,317,189 | B2 | 1/2008 | Miyazaki et al. |
| 2005/0253078 | A1 * | 11/2005 | Miyazaki et al. ...... 250/370.09 |

FOREIGN PATENT DOCUMENTS

JP 2006-15065 1/2006

* cited by examiner

*Primary Examiner* — Hoon Song
(74) *Attorney, Agent, or Firm* — Oblon, Spivak, McClelland, Maier & Neustadt, L.L.P.

(57) ABSTRACT

An X-ray CT apparatus has: a plurality of X-ray detection elements arranged in a matrix form; a QV amplifier unit having a plurality of QV amplifiers; a first connection unit connecting the plurality of X-ray detection elements and the QV amplifier unit; an AD converter unit having a plurality of AD converters; and a second connection unit connecting the QV amplifier unit and the AD converter unit. The plurality of X-ray detection elements and the QV amplifier unit are connected and the QV amplifier unit and the AD converter unit are connected so as to make different at least one of a signal processing characteristic of the QV amplifier unit and signal a processing characteristic of the AD converter unit for each X-ray detection element of the plurality of X-ray detection elements or for each of an adjacent plurality of X-ray detection elements.

5 Claims, 12 Drawing Sheets

X-RAY CT APPARATUS

BACKGROUND OF THE INVENTION

1. Field of the Invention

The present invention relates to an X-ray computed tomography (CT) technique for generating an image of an object by performing image reconstruction by detecting an X-ray transmitted through the object, and particularly, to an X-ray CT apparatus having a data acquisition system (DAS) and acquires information on an X-ray transmitted through the object required for image reconstruction as digital data.

2. Description of the Related Art

Recent X-ray CT apparatuses have an X-ray detector which is configured using an X-ray detection element array which is configured such that X-ray detection elements are two-dimensionally arranged. The X-ray detection element array has a tendency that the number of X-ray detection elements is increasing not only in a channel direction which is a rotational direction of the X-ray detector but also in a slice direction (line direction) which is crossed with the channel direction.

The X-ray CT apparatus is configured such that each X-ray detection element generates an X-ray detection signal (electrical signal), on which a DAS (see Japanese Patent Application Publication (Laid-open: KOKAI) No. 2006-15065 A) performs various kinds of signal processing such as a QV (Quantum of electric charge) conversion, an amplification, and an AD (Analog to Digital) conversion to generate projection data, which undergoes image reconstruction processing to produce a medical X-ray image, which appears on a display device.

FIG. 10 is a diagram illustrating a configuration example of a conventional X-ray CT apparatus.

FIG. 10 illustrates an X-ray detection element (PD) 9X and a DAS 6X of the conventional X-ray CT apparatus. FIG. 10 illustrates a configuration example in which 24 X-ray detection elements 9X on the X-ray detection element array share one QV chip (heavy lines in FIG. 10); and four X-ray detection elements 9X share one QV amplifier and one AD converter.

The DAS 6X has a QV amplifier unit 12X, an AD converter unit 13X, a first signal path 14X, and a second signal path 15X.

The QV amplifier unit 12X has QV chips as a plurality of IC chips and each QV chip has a plurality of QV amplifiers. FIG. 10 illustrates only a first QV chip having six QV amplifiers (QV 1 to QV 6) and a second QV chip having six QV amplifiers (QV 7 to QV 12). The X-ray detection element 9X detects a transmitted X-ray transmitted through the object and outputs an electrical signal reflecting an intensity of the transmitted X-ray. Each QV amplifier converts the electrical signal to a voltage signal and amplifies the voltage signal.

The AD converter unit 13X has a plurality of AD converters. FIG. 10 illustrates only twelve AD converters (ADC 1 to ADC 12). Each AD converter converts the voltage signal generated by a corresponding QV amplifier, to a digital signal.

The first signal path 14X forms a signal path starting at each X-ray detection element 9X and reaching the QV amplifier unit 12. The second signal path 15X forms a signal path connecting the QV amplifier unit 12X to the AD converter unit 13X. That is, the DAS 6X forms a signal path (starting at the first signal path 14X, passing through the QV amplifier unit 12X and the second signal path 15X, and reaching the AD converter unit 13X) for each X-ray detection element 9X, and acquires information on the transmitted X-ray as digital data.

Here, for the purpose of simplified structure, the DAS 6X is configured such that 24 (M=24) X-ray detection elements 9X continuing in a channel direction in the same line share one QV chip of the QV amplifier unit 12X. An X-ray detection element 9X in the m-th (m=1, 2, ..., M) channel and the n-th (n=1, 2, ..., N) line is expressed as an element [m, n]. For example, as illustrated in FIG. 10, the elements [1, 1] to [24, 1] share one QV chip.

Moreover, for the purpose of simplified structure, the DAS 6X is configured such that four X-ray detection elements 9X continuing in the channel direction and in the same line share one QV amplifier of the QV amplifier unit 12X. For example, as illustrated in FIG. 10, elements [1, 1] to [4, 1] share a QV 1 of the QV amplifier unit 12X.

Further, for the purpose of simplified structure, the DAS 6X is configured such that four X-ray detection elements 9X continuing in the channel direction and in the same line share one AD converter of the AD converter unit 13X. For example, as illustrated in FIG. 10, elements [1, 1] to [4, 1] share one ADC 1 of the AD converter unit 13X.

In general, the DAS 6X is configured such that signal processing characteristics differ for each circuit of the QV amplifier and the AD converter. Therefore, if a shared structure is used in which a QV amplifier is shared by the four X-ray detection elements 9X continuing in the channel direction and in the same line, the same QV amplifier has the same signal processing characteristics. Note that the DAS 6X is configured such that signal processing characteristics differ widely for each IC chip of a QV chip and the like. Therefore, if a shared structure is used in which a QV chip is shared by the 24 channels of X-ray detection elements 9X in the same line, signal processing characteristics differ widely between the two QV amplifiers (e.g., QV 1 and QV 7) each belonging to a different QV chip; while signal processing characteristics differ slightly (are similar) between the two QV amplifiers (e.g., QV 1 and QV 2) both belonging to the same QV chip.

FIGS. 11 and 12 are diagrams each illustrating a configuration example of a conventional X-ray CT apparatus.

FIGS. 11 and 12 each illustrate an X-ray detection element 9Y and a DAS 6Y of the conventional X-ray CT apparatus. FIGS. 11 and 12 each illustrate a structure example in which 16 X-ray detection elements 9Y on an X-ray detection element array share one QV chip (heavy lines in FIGS. 11 and 12); four X-ray detection elements 9Y share one AD chip (heavy lines in FIGS. 11 and 12); and one X-ray detection element 9Y corresponds to one QV amplifier and one AD converter.

The DAS 6Y has a QV amplifier unit 12Y, an AD converter unit 13Y, a first signal path 14Y, and a second signal path 15Y.

Here, the DAS 6Y is configured such that 16 (N=16) X-ray detection elements 9Y continuing in a line direction in the same channel share one QV chip of the QV amplifier unit 12Y. For example, as illustrated in FIG. 11, elements [1, 1] to [1, 16] share one QV chip.

In addition, the DAS 6Y is configured such that four X-ray detection elements 9Y continuing in the line direction in the same channel share one AD chip of the AD converter unit 13Y. For example, as illustrated in FIG. 11, elements [1, 1] to [1, 4] share one AD chip.

Moreover, the DAS 6Y is configured such that one X-ray detection element 9Y corresponds to only one QV amplifier. For example, as illustrated in FIG. 11, only element [1, 1] shares a QV 1 of the QV amplifier unit 12Y.

Further, the DAS 6Y is configured such that one X-ray detection element 9X corresponds to only one AD converter. For example, as illustrated in FIG. 11, only element [1, 1] corresponds to ADC 1 of the AD converter unit 13Y.

In general, the DAS 6X and 6Y illustrated in FIGS. 10 to 12 is configured such that signal processing characteristics differ widely for each IC chip of a QV chip and the like. Therefore, if a shared structure is used in which a QV chip is shared by the plurality of X-ray detection elements 9X, signal processing characteristics differ widely between the two QV amplifiers (e.g., QV 1 and QV 7 illustrated in FIG. 10) each belonging to a different QV chip; while signal processing characteristics are similar between the two QV amplifiers (e.g., QV 1 and QV 2 illustrated in FIG. 10) both belonging to the same QV chip.

More specifically, the DAS 6X illustrated in FIG. 10 is configured such that processing is performed on a group of four X-ray detection elements 9X continuing in the channel direction and in the same line on the X-ray detection element array under the same signal processing characteristics. In addition, the DAS 6X is configured such that a group adjacent to the above-mentioned group is signal-processed by the same QV chip, and thus processing is performed under similar signal processing characteristics. Moreover, the DAS 6X illustrated in FIG. 10 is configured such that a group of four X-ray detection elements 9X continuing in the channel direction and in the same line on the X-ray detection element array is signal-processed by the same QV chip and the same AD chip, and thus processing is performed under similar signal processing characteristics. Therefore, the DAS 6X and 6Y illustrated in FIGS. 10 to 12 cause an uneven distribution of signal processing characteristics on the X-ray detection element array, and thus artifacts are likely to appear noticeably.

Third-generation X-ray CT apparatuses are configured such that a channel of an X-ray detection element array is used in a fold back manner by sandwiching a channel at a center of field of view (FOV). At this time, in a channel region (particularly, 10-channel to 20-channel) near the center, the channel used in a fold back manner is restricted, and thus, artifacts due to an uneven distribution of signal processing characteristics of the DAS are likely to appear noticeably.

In recent years, image reconstruction performed by one scan using a widely used multi-line X-ray detection element array tends to produce such noticeable artifacts, and thus anti-artifact measures are required. As a method of removing such artifacts, a method can be considered of equalizing all signal processing characteristics of the QV chips, AD chips, QV amplifiers, AD converters, and the like constituting the DAS. However, the method is very difficult under the present technology and inevitably increases the cost of the X-ray CT apparatus and thus is unrealistic.

SUMMARY OF THE INVENTION

In view of the above circumstances, the present invention has been made, and a purpose of the present invention is to provide an X-ray CT apparatus capable of reducing artifacts caused by a variation of signal processing characteristics without equalizing signal processing characteristics of each signal path of a DAS if a shared structure of signal paths in the DAS is used.

To solve the above-described problems, the present invention provides the X-ray CT apparatus comprising: a plurality of X-ray detection elements arranged in a matrix form; a QV amplifier unit having a plurality of QV amplifiers; a first connection unit connecting the plurality of X-ray detection elements and the QV amplifier unit; an AD converter unit having a plurality of AD converters; and a second connection unit connecting the QV amplifier unit and the AD converter unit, wherein the plurality of X-ray detection elements and the QV amplifier unit are connected and the QV amplifier unit and the AD converter unit are connected so as to make different at least one of a signal processing characteristic of the QV amplifier unit and signal a processing characteristic of the AD converter unit for each X-ray detection element of the plurality of X-ray detection elements or for each of an adjacent plurality of X-ray detection elements.

DETAILED DESCRIPTION OF THE PREFERRED EMBODIMENTS

Embodiments of an X-ray CT apparatus according to the present invention will be described by referring to the accompanying drawings.

First Embodiment

Figure 1:
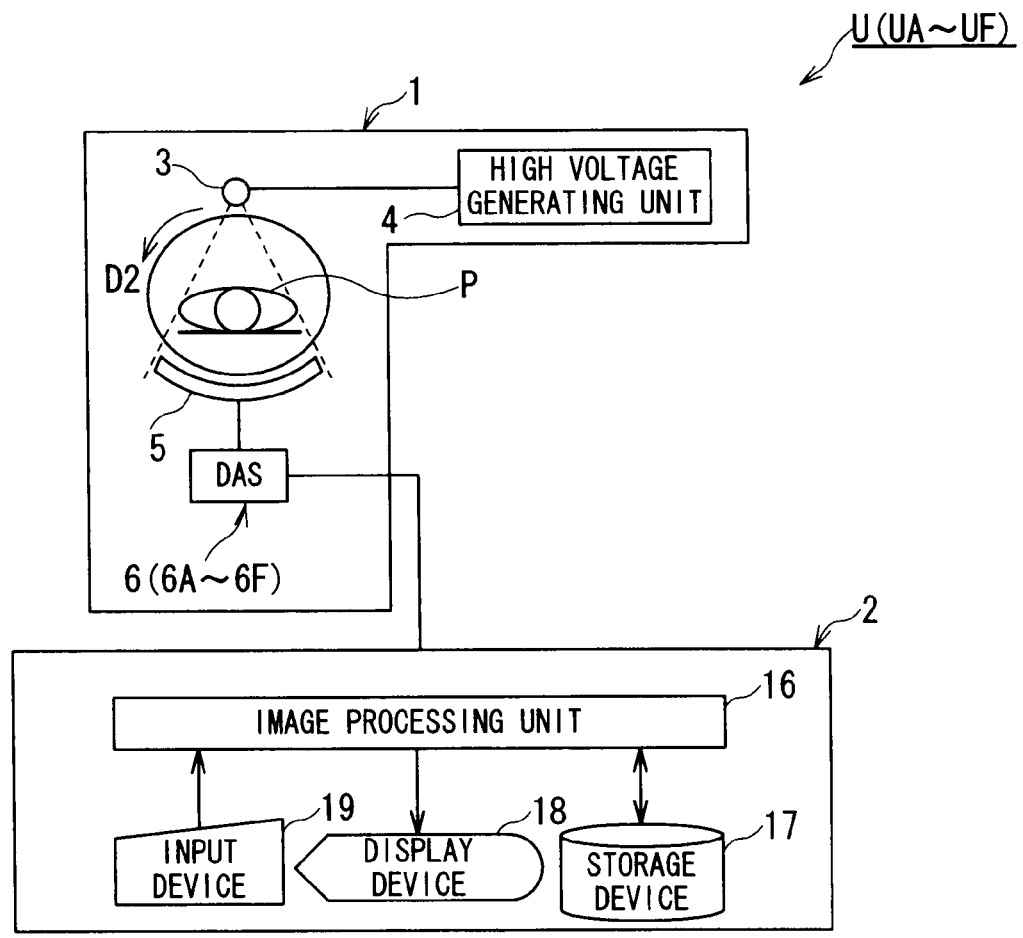
FIG. 1 is a schematic diagram illustrating a configuration of X-ray CT apparatus of each first embodiment to seventh embodiment.
Figure 2:
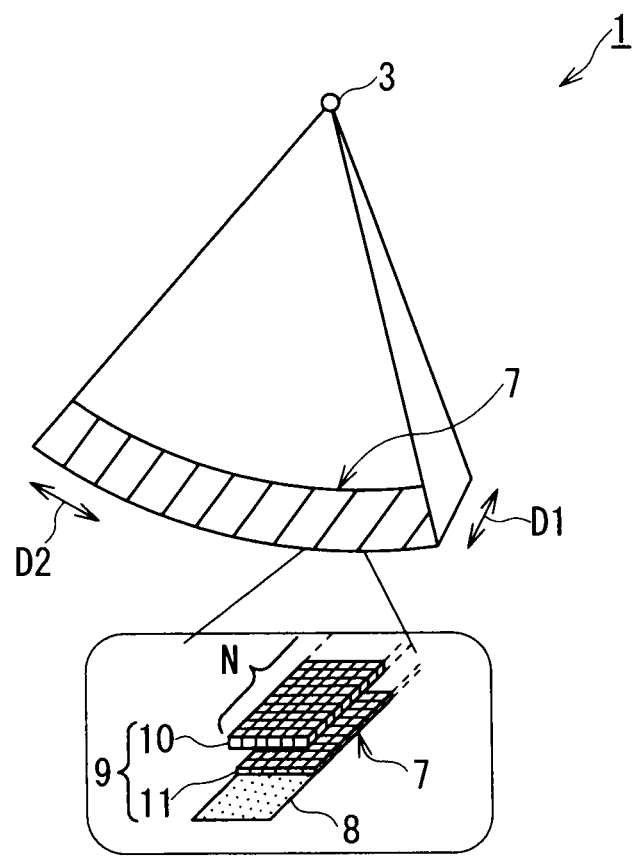
FIG. 2 is a partially detailed diagram illustrating the X-ray CT apparatus, illustrated in FIG. 1, of each first embodiment to seventh embodiment.

FIG. 1 is a schematic diagram illustrating a configuration of an X-ray CT apparatus of a first embodiment. FIG. 2 is a partially detailed diagram illustrating the X-ray CT apparatus of the first embodiment.

An X-ray CT apparatus U of the present embodiment includes a gantry (rotary frame) 1 and a console 2. The gantry 1 has an X-ray tube 3, a high voltage generating unit 4, an X-ray detector 5, and a data acquisition system (DAS) 6.

The X-ray tube 3 and the X-ray detector 5 are arranged facing each other and sandwiching an object P placed on a bed device (not illustrated) therebetween. Further, the X-ray tube 3 and the X-ray detector 5 are rotatably arranged in a channel direction D2 substantially orthogonal to a body axial direction (slice direction D1: see FIG. 2) of the object P.

The X-ray tube 3 receives a required tube voltage from the remote-controlled high voltage generating unit 4 and emits an X-ray having energy according to the received tube voltage from an arbitrary rotational position in a 360° rotational direction toward the object P.

Figure 3:
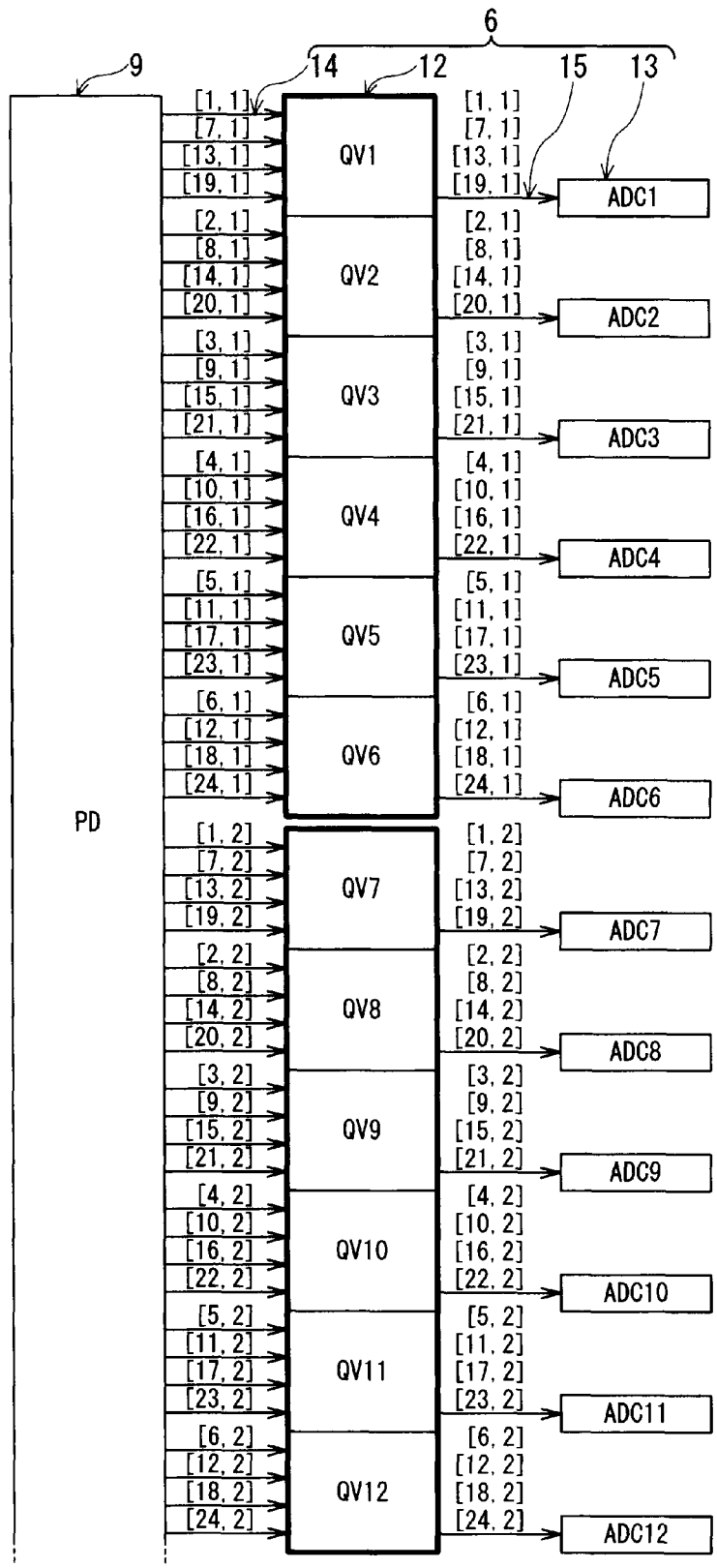
FIG. 3 is a diagram illustrating a configuration of a DAS according to the X-ray CT apparatus of the first embodiment.
Figure 4:
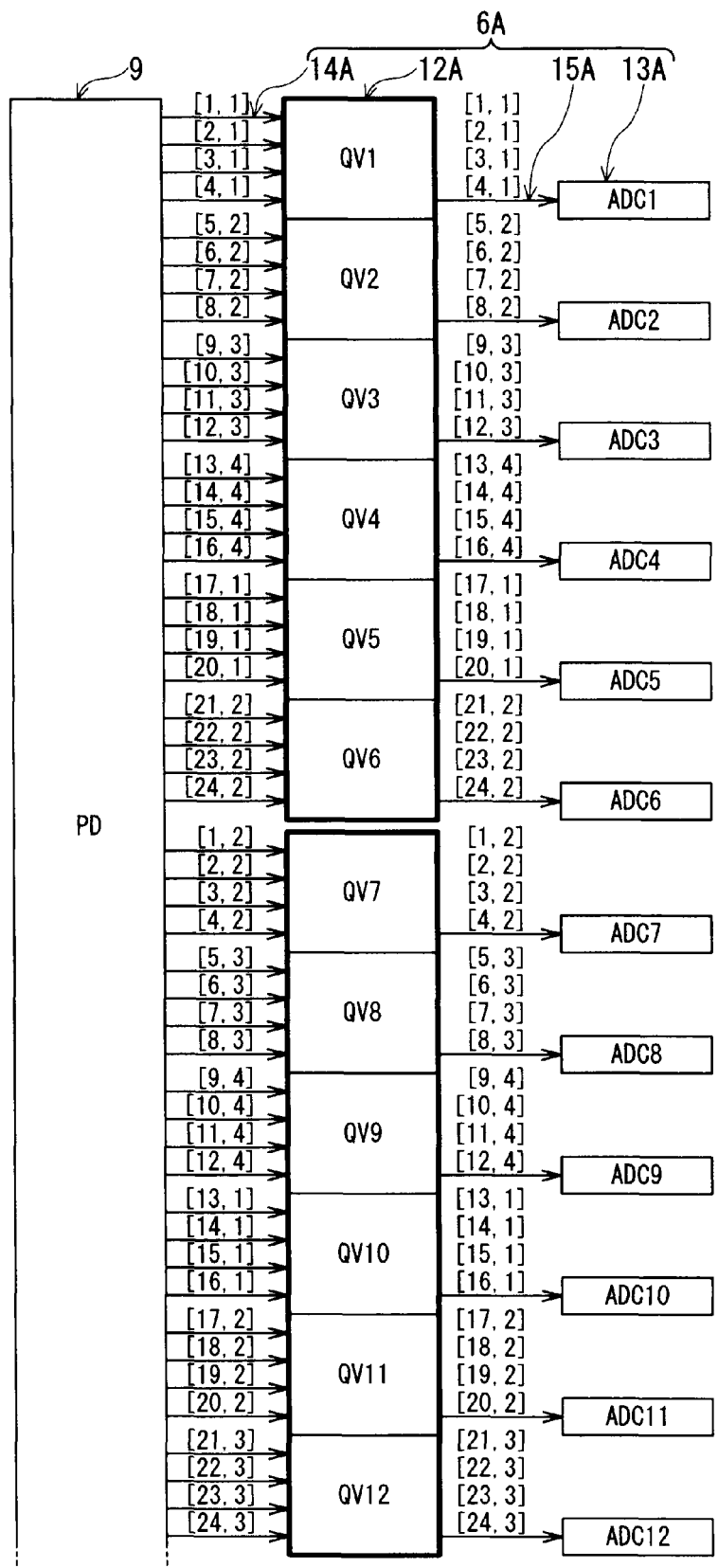
FIG. 4 is a diagram illustrating a configuration of a DAS according to the X-ray CT apparatus of the second embodiment.
Figure 5:
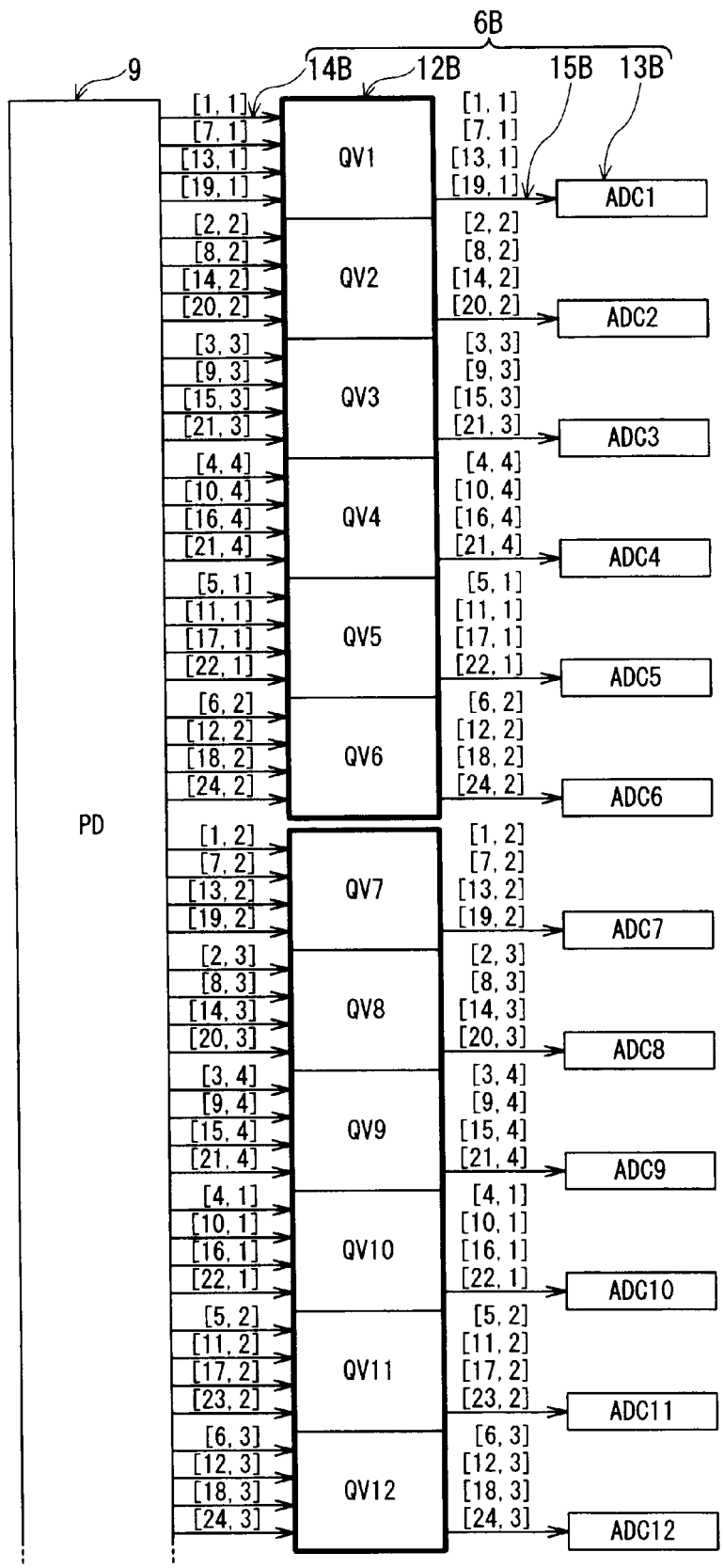
FIG. 5 is a diagram illustrating a configuration of a DAS according to the X-ray CT apparatus of the third embodiment.

The X-ray detector 5 is configured such that a plurality of X-ray detection element arrays 7 is tightly arranged in an arc shape and in a channel direction. Each X-ray detection element array 7 is configured such that a plurality of X-ray detection elements 9 is two-dimensionally arranged on a printed circuit board (PCB) substrate 8. Note that each X-ray detection element array 7 includes X-ray detection elements 9 having M (M=1, 2, ...) channels in the channel direction D2 and N (N=1, 2, ...) lines in the slice direction D1. Hereinafter, an X-ray detection element 9 included in one X-ray detection element array 7 in the m-th (m=1, 2, ..., M) channel and the n-th (n=1, 2, ..., N) lines is expressed as an element [m, n]. In FIGS. 3 to 5, the description focuses on one X-ray detection element array 7 in which X-ray detection elements 9 are arranged for 24 (M=24) channels in the channel direction D2. In FIGS. 6 to 9, the description focuses on one X-ray detection element array 7 in which X-ray detection elements 9 are arranged for 24 (M=24) channels in the channel direction D2, and for 16 (N=16) lines in the slice direction D1.

Each X-ray detection element 9 of the X-ray detector 5 is made of a pair of a scintillator 10 and a photodiode 11. Each X-ray detection element 9 detects an X-ray emitted from the X-ray tube 3 and transmitted through the object P, and generates an electrical signal reflecting an intensity of the transmitted X-ray. Each X-ray detection element 9 is independently connected to the DAS 6. Note that the scintillator 10 has a function to convert an X-ray incident on the X-ray detection element 9 to light and supply the light to the photodiode 11. The photodiode 11 has a function to convert the light received from the scintillator 10 to an X-ray detection signal (electrical signal).

FIG. 3 is a diagram illustrating a configuration of the DAS 6 according to the X-ray CT apparatus U of the first embodiment. Note that FIG. 3 illustrates a part of the DAS 6, namely, a part connected to one X-ray detection element array 7 (a total of 24 channels) if the number of channels is 24.

FIG. 3 illustrates the X-ray detection element (PD) 9 and the DAS 6 of the X-ray CT apparatus U. FIG. 3 illustrates a configuration example in which 24 X-ray detection elements 9 on the X-ray detection element array 7 share one QV chip (heavy lines in FIG. 3); and four X-ray detection elements 9 share one QV amplifier and one AD converter. The DAS 6 has a QV amplifier unit 12, an AD converter unit 13, a first signal path 14, and a second signal path 15.

Figure 10:
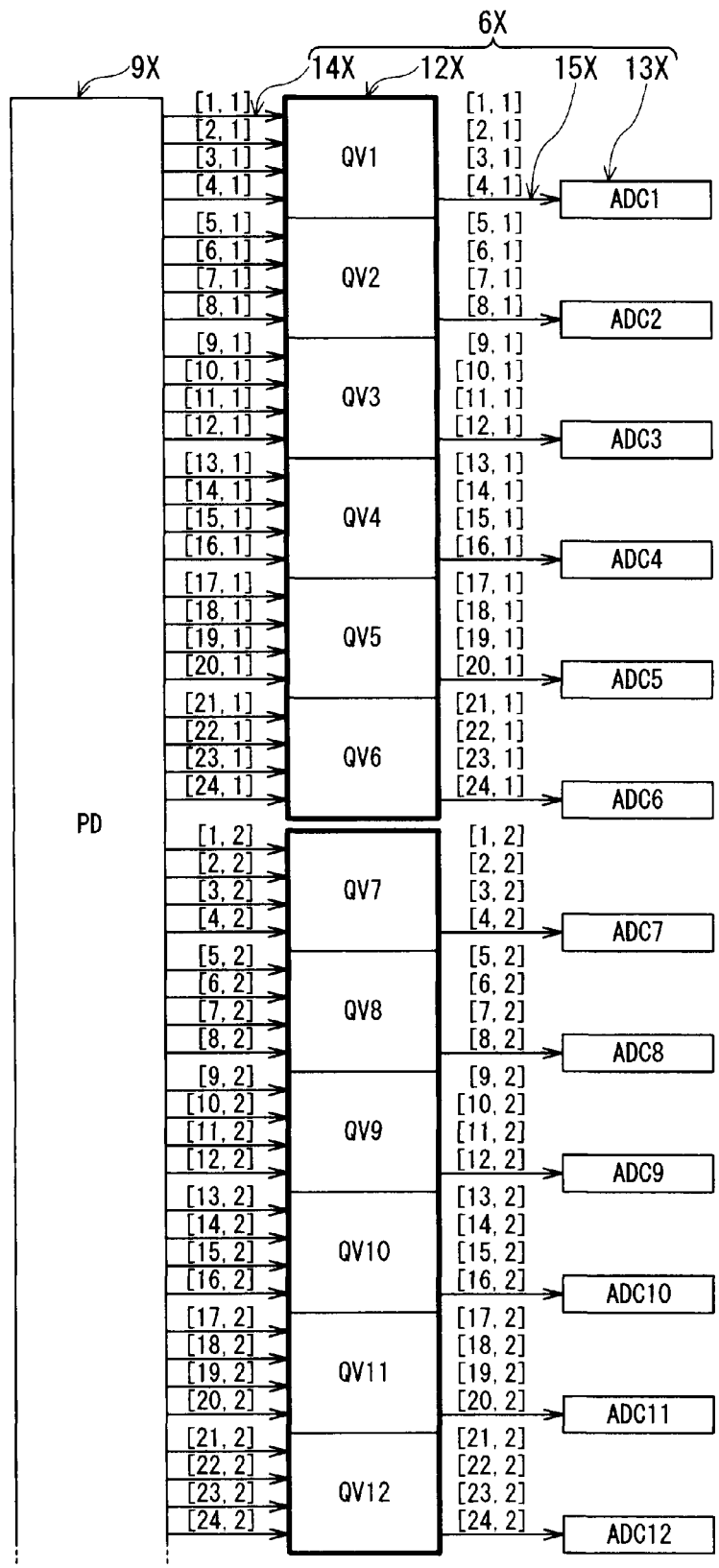
FIG. 10 is a diagram illustrating a configuration example of a conventional X-ray CT apparatus.

The DAS 6 allocates 24 X-ray detection elements 9 in the same line to one QV chip. In addition, the DAS 6 allocates four unadjacent X-ray detection elements 9 to one QV amplifier. In addition, the DAS 6 allocates four unadjacent X-ray detection elements 9 to one AD converter. Consequently, the DAS 6 allocates QV chips for each line in the same manner as the conventional DAS 6X (illustrated in FIG. 10), but adjacent X-ray detection elements 9 are processed by a different circuit in the same QV chip. As a result, the DAS 6 can distribute signal processing characteristics on the X-ray detection element array 7 in such a manner that adjacent X-ray detection elements 9 have non-identical signal processing characteristics.

The QV amplifier unit 12 has QV chips as a plurality of IC chips and each QV chip has a plurality of QV amplifiers. FIG. 3 illustrates only a first QV chip having six QV amplifiers (QV 1 to QV 6) and a second QV chip having six QV amplifiers (QV 7 to QV 12). Each photodiode 11 of the X-ray detection elements 9 outputs an X-ray detection signal as an electrical signal. Each QV amplifier converts the electrical signal to a voltage signal and amplifies the voltage signal.

The AD converter unit 13 has a plurality of AD converters. FIG. 3 illustrates only twelve AD converters (ADC 1 to ADC 12). Each AD converter converts the voltage signal generated by a corresponding QV amplifier, to a digital signal.

The first signal path 14 forms a signal path starting at each X-ray detection element 9 and reaching the QV amplifier unit 12. The second signal path 15 forms a signal path connecting the QV amplifier unit 12 to the AD converter unit 13. The signal paths (not illustrated) following the AD converter unit 13 reach console 2. That is, the DAS 6 forms a signal path reaching the console 2 for each X-ray detection element 9, and acquires projection information of the X-ray detection signal generated by the transmitted X-ray as digital data (projection data).

For example, the DAS 6 allocates four X-ray detection elements 9 in the same line and not continuing in the channel direction, to one QV amplifier as well as to one AD converter. Therefore, if 10 lines of X-ray detection elements 9 are arranged in the X-ray detection element array 7, the X-ray detection element array 7 has 60 QV amplifiers and 60 AD converters.

Specifically, as illustrated in FIG. 3, the DAS 6 is configured such that the elements [1, 1] to [24, 1] in the first line share one QV chip. As illustrated in FIG. 3, the DAS 6 is configured such that the elements [1, 2] to [24, 2] in the second line share one QV chip.

As illustrated in FIG. 3, the DAS 6 is configured such that elements [1, 1], [7, 1], [13, 1], and [19, 1] share QV 1 and ADC 1. The DAS 6 is configured such that elements [2, 1], [8, 1], [14, 1], and [20, 1] share QV 2 and ADC 2. The DAS 6 is configured such that elements [3, 1], [9, 1], [15, 1], and [21, 1] share QV 3 and ADC 3. The DAS 6 is configured such that elements [4, 1], [10, 1], [16, 1], and [22, 1] share QV 4 and ADC 4. The DAS 6 is configured such that elements [5, 1], [11, 1], [17, 1], and [23, 1] share QV 5 and ADC 5. The DAS 6 is configured such that elements [6, 1], [12, 1], [18, 1], and [24, 1] share QV 6 and ADC 6.

Note that the number of X-ray detection elements 9 sharing each QV amplifier and each AD converter is not limited to 4.

The console 2 includes an image processing unit 16, a storage device 17, a display device 18, and an input device 19. Based on various programs stored in the storage device 17, the image processing unit 16 executes image processing for generating a desired slice thickness of image data from the projection data received from the DAS 6 and displays an X-ray image on the display device 18. An operator can supply a necessary instruction to a system control unit (not illustrated) for performing various controls required for scanning via the input device 19.

Hereinafter, an operation of the X-ray CT apparatus U will be described.

According to the conventional DAS 6X (illustrated in FIG. 10), each X-ray detection signal generated by the 24 channels of elements [1, 1] to [24, 1] in the same line is signal-processed by the same QV chip. In other words, each X-ray detection signal generated by the elements [1, 1] to [24, 1] is signal-processed under similar signal processing characteristics. In addition, according to the DAS 6X, each X-ray detection signal generated by the four elements [1, 1] to [4, 1] continuing in the channel direction and in the same line is signal-processed by the same QV 1 and the same ADC 1. In other words, each X-ray detection signal generated by the four elements [1, 1] to [4, 1] is signal-processed under the same signal processing characteristics. Consequently, the DAS 6X causes an uneven distribution of signal processing characteristics, and thus artifacts are likely to appear noticeably.

In contrast to this, according to the DAS 6 of the X-ray CT apparatus U, of the four elements [1, 1] to [4, 1] continuing in the channel direction and in the same line, the X-ray detection signal generated by the element [1, 1] is signal-processed by the QV 1 and the ADC 1; the X-ray detection signal generated by the element [2, 1] is signal-processed by the QV 2 and the ADC 2; the X-ray detection signal generated by the element [3, 1] is signal-processed by the QV 3 and the ADC 3; and the X-ray detection signal generated by the element [4, 1] is signal-processed by the QV 4 and the ADC 4. That is, according to the DAS 6, each X-ray detection signal generated by adjacent X-ray detection elements 9 is signal-processed by a different QV amplifier in the same QV chip and a different AD converter. Therefore, the signal processing characteristics of the X-ray detection signals generated by the adjacent X-ray detection elements 9 may be similar, but is not the same.

Hereinafter, advantages of the X-ray CT apparatus U will be described.

The DAS 6 of the X-ray CT apparatus U has a characteristic distribution connection structure in which adjacent X-ray detection elements 9 have non-identical signal processing characteristics. Consequently, the X-ray CT apparatus U can reduce the uneven distribution of signal processing characteristics of the DAS 6 and can reduce artifacts caused by a variation of signal processing characteristics without equalizing the signal processing characteristics on the X-ray detection element array 7.

Second Embodiment

The schematic configuration view of an X-ray CT apparatus UA of a second embodiment is the same as FIG. 1 and the partially detailed view is the same as FIG. 2.

FIG. 4 is a diagram illustrating a configuration of a DAS 6A of the X-ray CT apparatus UA according to the second embodiment. The DAS 6A of the X-ray CT apparatus UA of the second embodiment is a modified example of the DAS 6 illustrated in FIG. 3. Note that in FIG. 4, the description is made by adding "A" to the end of the reference numeral or character of a component modifying or newly added to a corresponding component of FIG. 3.

FIG. 4 illustrates an X-ray detection element (PD) 9 and a DAS 6A of the X-ray CT apparatus UA. The DAS 6A has a QV amplifier unit 12A, an AD converter unit 13A, a first signal path 14A, and a second signal path 15A.

The DAS 6A allocates a group consisting of four X-ray detection elements 9 continuing in the channel direction and in the same line, to one QV chip (heavy lines in FIG. 4). In addition, the DAS 6A allocates a group consisting of four X-ray detection elements 9 unadjacent to the above-mentioned group and continuing in the channel direction, to one QV chip. Consequently, the DAS 6A is configured to process the X-ray detection elements 9 in a group by the same circuit and the X-ray detection elements 9 belonging to adjacent groups by a different QV chip. As a result, the DAS 6A can distribute the signal processing characteristics of adjacent groups on the X-ray detection element array 7 in such a manner that the adjacent groups of X-ray detection elements 9 have non-identical, non-similar, widely different signal processing characteristics.

Specifically, as illustrated in FIG. 4, the DAS 6A is configured such that one QV chip is shared by the elements [1, 1] to [4, 1] in the first line, the elements [5, 2] to [8, 2] in the second line, the elements [9, 3] to [12, 3] in the third line, the elements [13, 4] to [16, 4] in the fourth line, the elements [17, 1] to [20, 1] in the first line, and the elements [21, 2] to [24, 2] in the second line. Further, as illustrated in FIG. 4, the DAS 6A is configured such that one QV chip is shared by the elements [1, 2] to [4, 2], [5, 3] to [8, 3], [9, 4] to [12, 4], [13, 1] to [16, 1], [17, 2] to [20, 2], and [21, 3] to [24, 3].

In addition, as illustrated in FIG. 4, the DAS 6A is configured such that the elements [1, 1] to [4, 1] share QV 1 and ADC 1. The DAS 6A is configured such that the elements [5, 2] to [8, 2] share QV 2 and ADC 2. The DAS 6A is configured such that the elements [9, 3] to [12, 3] share QV 3 and ADC 3. The DAS 6A is configured such that the elements [13, 4] to [16, 4] share QV 4 and ADC 4. The DAS 6A is configured such that the elements [17, 1] to [20, 1] share QV 5 and ADC 5. The DAS 6A is configured such that the elements [21, 2] to [24, 2] share QV 6 and ADC 6.

Note that the DAS 6A is not limited to the configuration in which a group consists of four X-ray detection elements 9 continuing in the same line and in the channel direction. For example, a group may consist of four elements [1, 1] to [1, 4] in a different line and in the same channel or a group may consist of four elements [1, 1] to [2, 2] in a matrix form. Moreover, the number of X-ray detection elements 9 in a group is not limited to 4.

Hereinafter, an operation of the X-ray CT apparatus UA will be described.

According to the DAS 6A of the X-ray CT apparatus UA, the X-ray detection signals generated by a group of four elements [1, 1] to [4, 1] continuing in the channel direction and in the same line are signal-processed by the QV 1 of the first QV chip. The X-ray detection signals generated by another group of four elements [5, 1] to [8, 1] adjacent to the above-mentioned group are signal-processed by a QV chip different from the first QV chip. The X-ray detection signals generated by another group of four elements [1, 2] to [4, 2] adjacent to the above-mentioned group are signal-processed by the QV 7 of the second QV chip. That is, according to the DAS 6A, the X-ray detection signals generated within the same group have the same signal processing characteristics, but the X-ray detection signals generated by adjacent groups have non-identical, non-similar, widely different signal processing characteristics.

Hereinafter, advantages of the X-ray CT apparatus UA will be described.

The DAS 6A of the X-ray CT apparatus UA has a characteristic distribution connection structure in which adjacent groups of X-ray detection elements 9 have non-identical, non-similar, widely different signal processing characteristics. Consequently, the X-ray CT apparatus UA can reduce the uneven distribution of signal processing characteristics of the DAS 6A and can reduce artifacts caused by a variation of signal processing characteristics without equalizing the signal processing characteristics on the X-ray detection element array 7.

Third Embodiment

The schematic configuration view of an X-ray CT apparatus UB of a third embodiment is the same as FIG. 1 and the partially detailed view is the same as FIG. 2.

FIG. 5 is a diagram illustrating a configuration of the DAS 6B according to the X-ray CT apparatus UB of the third embodiment. The DAS 6B of the X-ray CT apparatus UB of the third embodiment is a modified example of the DAS 6 illustrated in FIG. 3. Note that in FIG. 5, the description is made by adding "B" to the end of the reference numeral or character of a component modifying or newly added to a corresponding component of FIG. 3.

FIG. 5 illustrates the X-ray detection element (PD) 9 and the DAS 6B of the X-ray CT apparatus UB. The DAS 6B has a QV amplifier unit 12B, an AD converter unit 13B, a first signal path 14B, and a second signal path 15B.

The DAS 6B allocates unadjacent four X-ray detection elements 9 to one QV amplifier (heavy lines in FIG. 5). In addition, the DAS 6B allocates unadjacent 24 X-ray detection elements 9 to one QV chip. In addition, the DAS 6B allocates unadjacent four X-ray detection elements 9 to one AD converter. Consequently, the DAS 6B processes adjacent X-ray detection elements 9 by a different circuit and a different QV chip. As a result, the DAS 6B can distribute the signal processing characteristics on the X-ray detection element array 7 in such a manner that the adjacent X-ray detection elements 9 have non-identical, non-similar, widely different signal processing characteristics.

Specifically, as illustrated in FIG. 5, the DAS 6B is configured such that the elements [1, 1], [7, 1], [13, 1], and [19, 1] in the first line share the QV 1 and the ADC 1. The DAS 6B is configured such that the elements [2, 2], [8, 2], [14, 2], and [20, 2] in the second line share the QV 2 and the ADC 2. The DAS 6B is configured such that the elements [3, 3], [9, 3], [15, 3], and [21, 3] in the third line share the QV 3 and the ADC 3. The DAS 6B is configured such that the elements [4, 4], [10, 4], [16, 4], and [22, 4] in the fourth line share the QV 4 and the ADC 4. The DAS 6B is configured such that the elements [5, 1], [11, 1], [17, 1], and [23, 1] in the first line share the QV 5 and the ADC 5. The DAS 6B is configured such that the elements [6, 2], [12, 2], [18, 2], and [24, 2] in the second line share the QV 6 and the ADC 6.

Note that the number of X-ray detection elements 9 sharing each QV amplifier and each AD converter is not limited to 4.

Hereinafter, an operation of the X-ray CT apparatus UB will be described.

According to the DAS 6B of the X-ray CT apparatus UB, the X-ray detection signal generated by the element [1, 1] on the X-ray detection element array 7 is signal-processed by the QV 1 and the ADC 1. The X-ray detection signal generated by the element [2, 1] on the X-ray detection element array 7 and the X-ray detection signal generated by the element [1, 2] are signal-processed by a QV chip different from the QV chip of the element [1, 1] and an AD converter different from the ADC 1. That is, according to the DAS 6B, the X-ray detection signals generated by the adjacent X-ray detection elements 9 have non-identical, non-similar, widely different signal processing characteristics.

Hereinafter, advantages of the X-ray CT apparatus UB will be described.

The DAS 6B of the X-ray CT apparatus UB has a characteristic distribution connection structure in which adjacent X-ray detection elements 9 have non-identical, non-similar, widely different signal processing characteristics. Consequently, the X-ray CT apparatus UB can reduce artifacts caused by a variation of signal processing characteristics without equalizing the signal processing characteristics on the X-ray detection element array 7. Moreover, in comparison with the DAS 6 of the X-ray CT apparatus U of the first embodiment and the DAS 6A of the X-ray CT apparatus UA of the second embodiment, the X-ray CT apparatus UB can well reduce the uneven distribution of signal processing characteristics of the DAS 6B, and thus artifacts are more difficult to appear noticeably.

Fourth Embodiment

The schematic configuration view of an X-ray CT apparatus UC of a fourth embodiment is the same as FIG. 1 and the partially detailed view is the same as FIG. 2.

Figure 6:
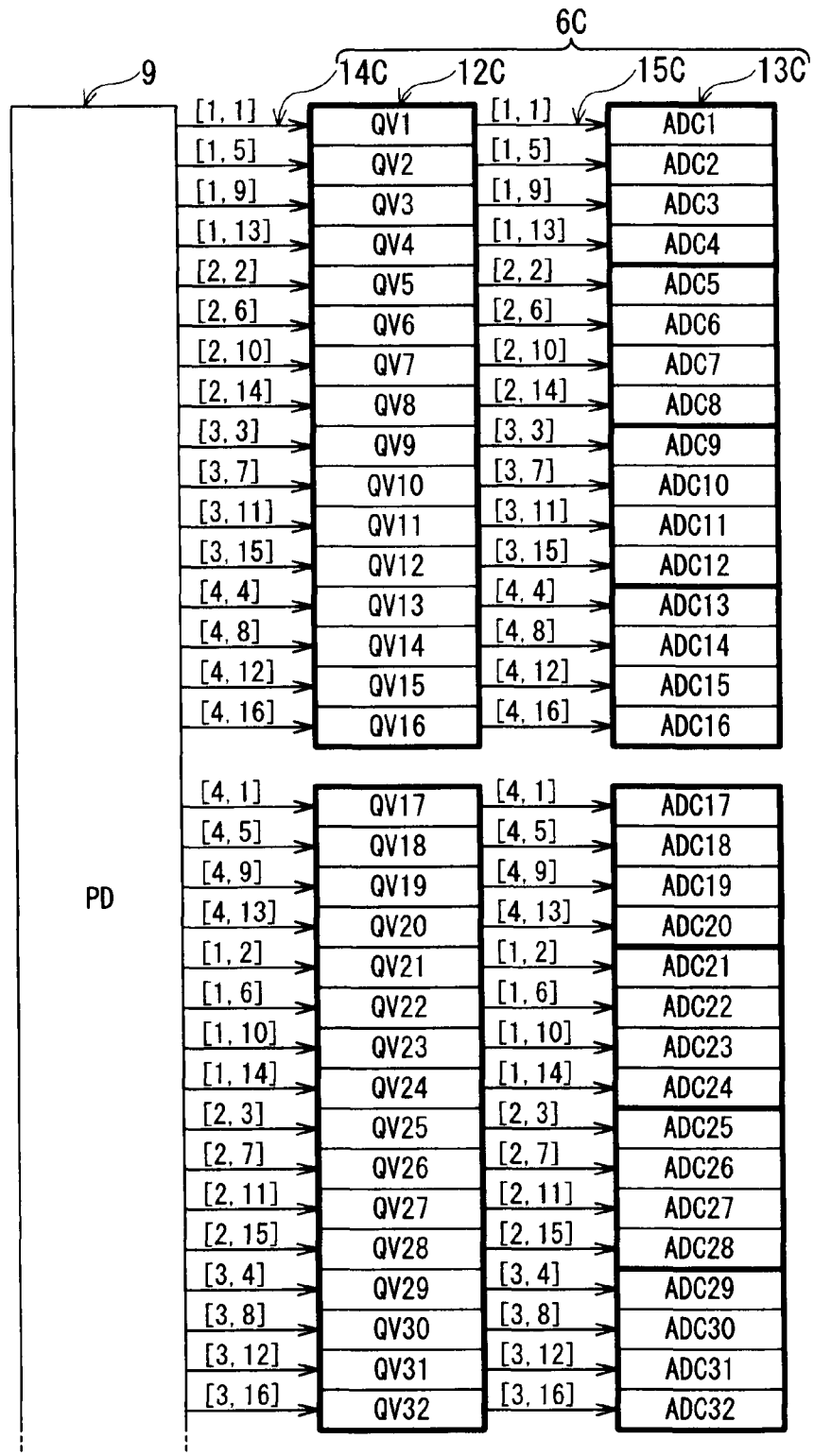
FIG. 6 is a diagram illustrating a configuration of a DAS according to the X-ray CT apparatus of the fourth embodiment.

FIG. 6 is a diagram illustrating a configuration of the DAS 6C according to the X-ray CT apparatus UC of the fourth embodiment.

FIG. 6 illustrates the X-ray detection element (PD) 9 and the DAS 6C of the X-ray CT apparatus UC. FIG. 6 illustrates a configuration example in which 16 X-ray detection elements 9 on the X-ray detection element array 7 share one QV chip (heavy lines in FIG. 6); four X-ray detection elements 9 share one AD chip (heavy lines in FIG. 6); and one X-ray detection element 9 corresponds to one QV amplifier and one AD converter. The DAS 6C has a QV amplifier unit 12C, an AD converter unit 13C, a first signal path 14C, and a second signal path 15C.

The DAS 6C allocates 16 unadjacent X-ray detection elements 9 to one QV chip. In addition, the DAS 6C allocates four unadjacent X-ray detection elements 9 to one AD chip. Consequently, the DAS 6C is configured to process adjacent X-ray detection elements 9 by a different QV chip and a different AD chip. As a result, the DAS 6C can distribute signal processing characteristics on the X-ray detection element array 7 in such a manner that adjacent X-ray detection elements 9 have non-identical, non-similar, widely different signal processing characteristics.

The QV amplifier unit 12C has QV chips as a plurality of IC chips and each QV chip has a plurality of QV amplifiers. FIG. 6 illustrates only a first QV chip having 16 QV amplifiers (QV 1 to QV 16) and a second QV chip having 16 QV amplifiers (QV 17 to QV 32). Each photodiode 11 of the X-ray detection elements 9 outputs an X-ray detection signal as an electrical signal. Each QV amplifier converts the electrical signal to a voltage signal and amplifies the voltage signal.

The AD converter unit 13C has AD chips as a plurality of IC chips, and each AD chip has a plurality of AD converters. FIG. 6 illustrates a first AD chip having four AD converters (ADC 1 to ADC 4), a second AD chip having four AD converters (ADC 5 to ADC 8), and so on. Each AD converter converts a voltage signal generated by a QV amplifier to a digital signal.

The first signal path 14C forms a signal path starting at each X-ray detection element 9 and reaching the QV amplifier unit 12C. The second signal path 15C forms a signal path connecting the QV amplifier unit 12C to the AD converter unit 13C.

Specifically, as illustrated in FIG. 6, the DAS 6C is configured such that one QV chip is shared by the unadjacent elements [1, 1], [1, 5], [1, 9], and [1, 13] in the first channel, the unadjacent elements [2, 2], [2, 6], [2, 10], and [2, 14] in the second channel, the unadjacent elements [3, 3], [3, 7], [3, 11], and [3, 15] in the third channel, and the unadjacent elements [4, 4], [4, 8], [4, 12], and [4, 16] in the fourth channel. As illustrated in FIG. 6, the DAS 6C is configured such that one AD chip is shared by the unadjacent elements [1, 1], [1, 5], [1, 9], and [1, 13] in the first channel.

Hereinafter, an operation of the X-ray CT apparatus UC will be described.

Figure 11:
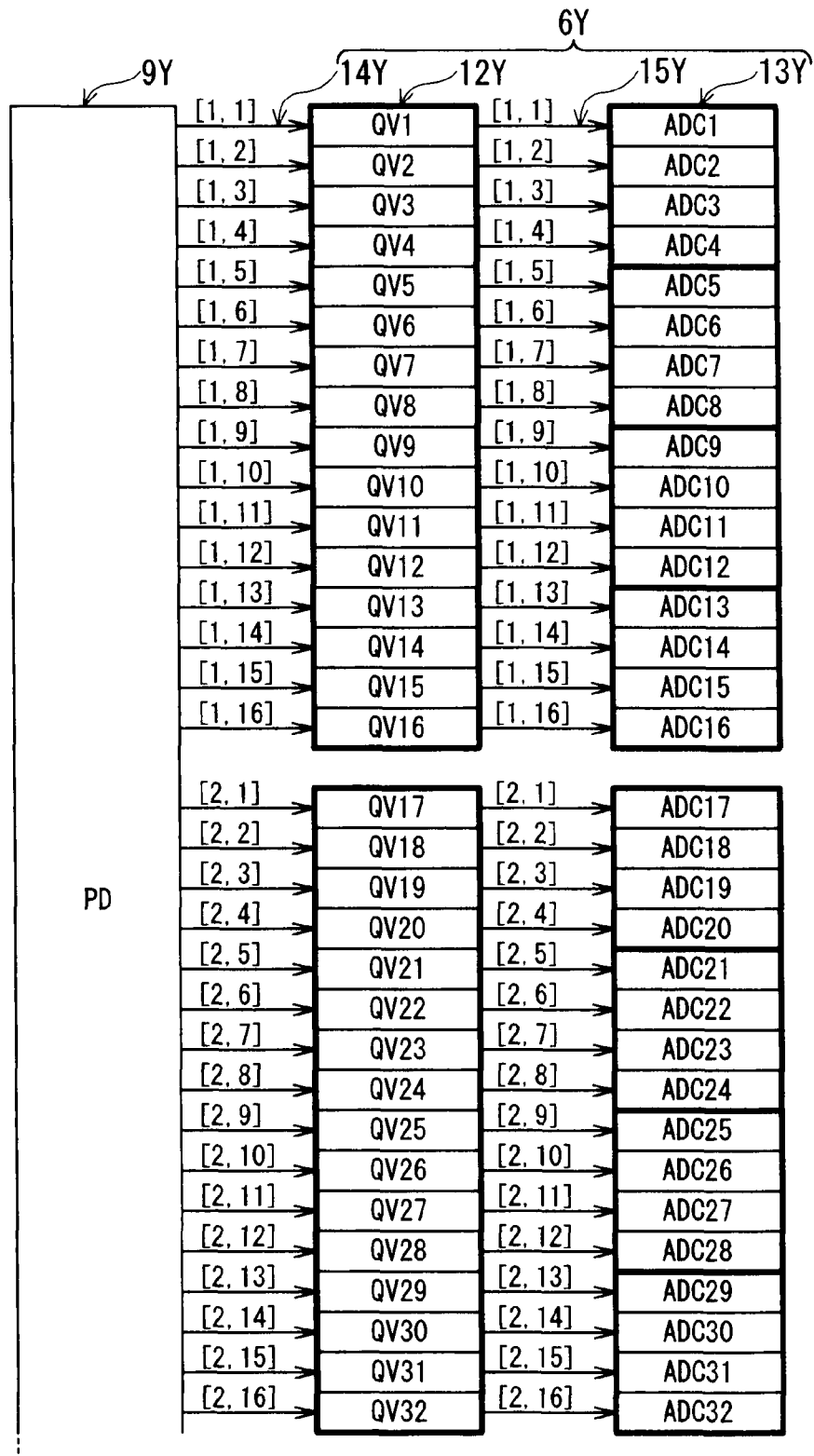
FIG. 11 is a diagram illustrating a configuration example of a conventional X-ray CT apparatus.
Figure 12:
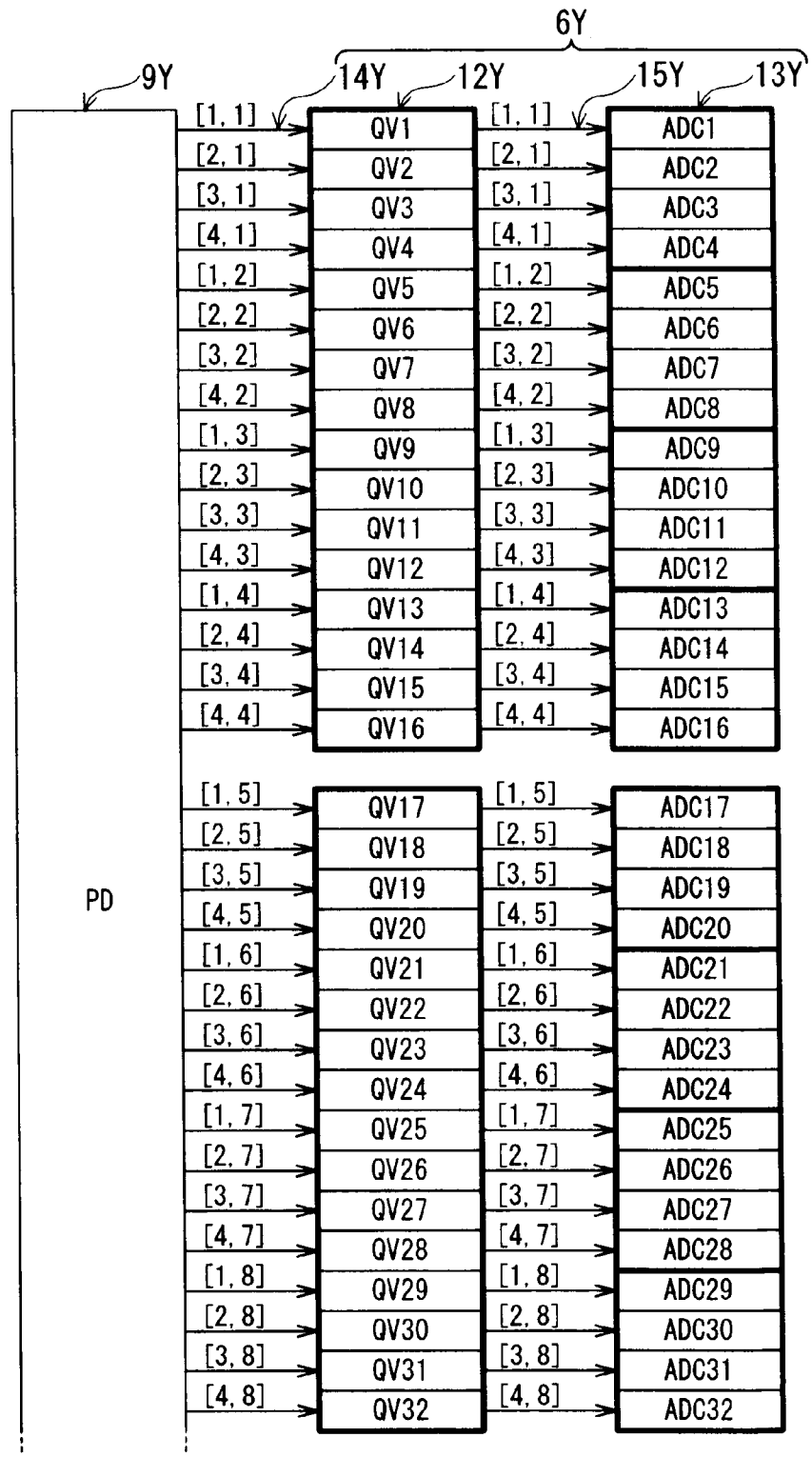
FIG. 12 is a diagram illustrating a configuration example of a conventional X-ray CT apparatus.

According to the conventional DAS 6Y (illustrated in FIGS. 11 and 12), each X-ray detection signal generated by four X-ray detection elements 9Y continuing in the channel direction and in the same line is signal-processed by the same QV chip and the same AD chip. In other words, each X-ray detection signal generated by the elements [1, 1] to [4, 1] and the elements [1, 1] to [1, 4] is signal-processed under similar signal processing characteristics. Consequently, the DAS 6Y causes an uneven distribution of signal processing characteristics, and thus artifacts are likely to appear noticeably.

In contrast to this, according to the DAS 6C of the X-ray CT apparatus UC, of the four adjacent elements [1, 1] to [4, 1], the X-ray detection signal generated by the element [1, 1] is signal-processed by the first QV chip and the first AD chip. The X-ray detection signal generated by the element [2, 1] is signal-processed by a QV chip different from the first QV chip and an AD chip different from the first AD chip. That is, according to the DAS 6C, the X-ray detection signals generated by adjacent X-ray detection elements 9 are signal-processed by a different QV chip and a different AD chip, and thus, the signal processing characteristics are non-identical, non-similar, and widely different.

Hereinafter, advantages of the X-ray CT apparatus UC will be described.

The DAS 6C of the X-ray CT apparatus UC has a characteristic distribution connection structure in which adjacent X-ray detection elements 9 have non-identical, non-similar, widely different signal processing characteristics. Consequently, the X-ray CT apparatus UC can reduce the uneven distribution of signal processing characteristics of the DAS 6C and can reduce artifacts caused by a variation of signal processing characteristics without equalizing the signal processing characteristics on the X-ray detection element array 7.

Fifth Embodiment

The schematic configuration view of an X-ray CT apparatus UD of a fifth embodiment is the same as FIG. 1 and the partially detailed view is the same as FIG. 2.

Figure 7:
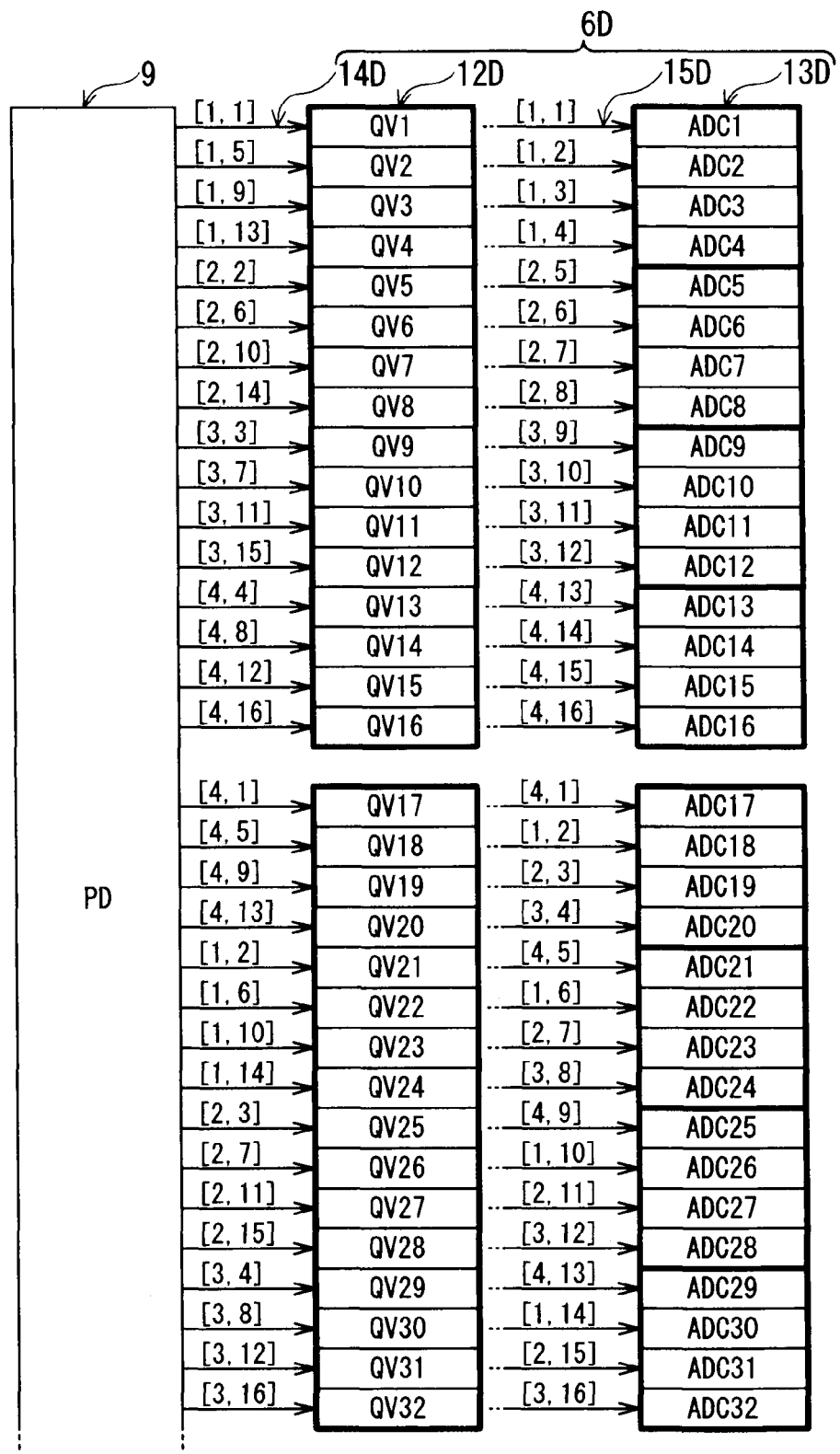
FIG. 7 is a diagram illustrating a configuration of a DAS according to the X-ray CT apparatus of the fifth embodiment.

FIG. 7 is a diagram illustrating a configuration of the DAS 6D according to the X-ray CT apparatus UD of the fifth embodiment. The DAS 6D of the X-ray CT apparatus UD of the fifth embodiment is a modified example of the DAS 6C illustrated in FIG. 6. Note that in FIG. 7, the description is made by adding "D" to the end of the reference numeral or character of a component modifying or newly added to a corresponding component of FIG. 6.

According to the DAS 6C of the X-ray CT apparatus UC illustrated in FIG. 6, unadjacent elements [1, 1], [1, 5], [1, 9], and [1, 13] are signal-processed by the same QV chip and are signal-processed by the same AD chip. In other words, unadjacent elements [1, 1], [1, 5], [1, 9], and [1, 13] have similar signal processing characteristics. However, the DAS 6D of the X-ray CT apparatus UD illustrated in FIG. 7 is configured such that even the unadjacent elements [1, 1], [1, 5], [1, 9], and [1, 13] are recombined between a combination of X-ray detection elements 9 to be processed by one QV chip and a combination of X-ray detection elements 9 to be processed by one AD chip so that the signal processing characteristics do not become similar.

For example, according to the DAS 6D, the element [1, 1] is combined with the elements [1, 5], [1, 9], and [1, 13] in the QV chip, but is combined with the elements [1, 2], [1, 3], and [1, 4] in the AD chip.

Hereinafter, advantages of the X-ray CT apparatus UD will be described.

The DAS 6D of the X-ray CT apparatus UD has a characteristic distribution connection structure in which adjacent X-ray detection elements 9 have non-identical, non-similar, widely different signal processing characteristics. Consequently, the X-ray CT apparatus UD can reduce the uneven distribution of signal processing characteristics of the DAS 6D and can reduce artifacts caused by a variation of signal processing characteristics without equalizing the signal processing characteristics on the X-ray detection element array 7. Moreover, in comparison with the DAS 6C of the X-ray CT apparatus UC of the fourth embodiment, the X-ray CT apparatus UD can well reduce the uneven distribution of signal processing characteristics of the DAS 6D, and thus artifacts are more difficult to appear noticeably.

Sixth Embodiment

The schematic configuration view of an X-ray CT apparatus UE of a sixth embodiment is the same as FIG. 1 and the partially detailed view is the same as FIG. 2.

Figure 8:
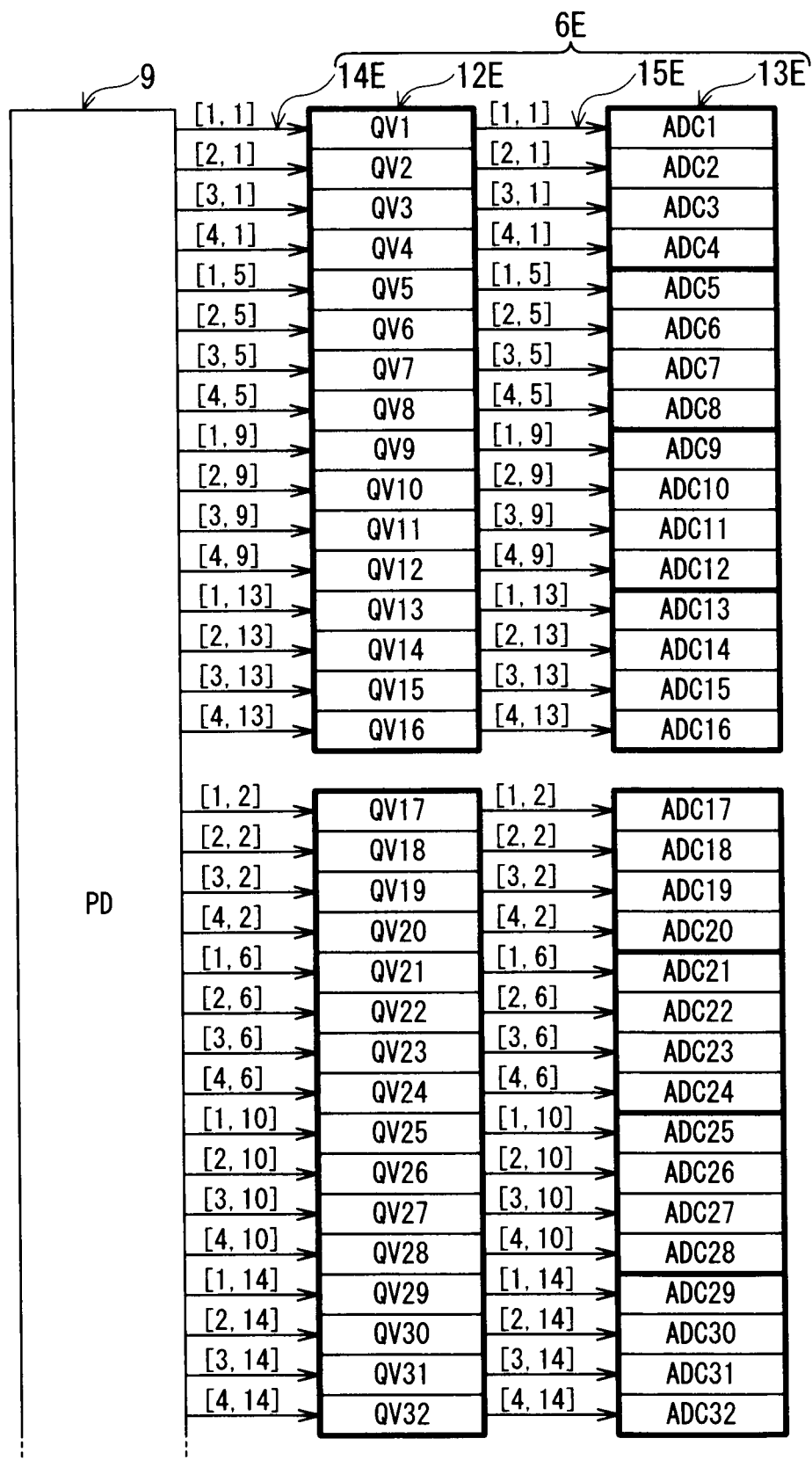
FIG. 8 is a diagram illustrating a configuration of a DAS according to the X-ray CT apparatus of the sixth embodiment.

FIG. 8 is a diagram illustrating a configuration of the DAS 6E according to the X-ray CT apparatus UE of the sixth embodiment.

FIG. 8 illustrates the X-ray detection element (PD) 9 and the DAS 6E of the X-ray CT apparatus UE. FIG. 8 illustrates a configuration example in which 16 X-ray detection elements 9 on the X-ray detection element array 7 share one QV chip (heavy lines in FIG. 8); four X-ray detection elements 9 share one AD chip (heavy lines in FIG. 8); and one X-ray detection element 9 corresponds to one QV amplifier and one AD converter. The DAS 6E has a QV amplifier unit 12E, an AD converter unit 13E, a first signal path 14E, and a second signal path 15E.

The DAS 6E allocates 16 X-ray detection elements 9 to one QV chip. In addition, the DAS 6E allocates four X-ray detection elements 9 to one AD chip. The DAS 6E includes a group consisting of four X-ray detection elements 9 continuing in the channel direction and in the same line, to one QV chip. In addition, the DAS 6E includes a group consisting of four X-ray detection elements 9 unadjacent to the above-mentioned group and continuing in the channel direction, to one QV chip. Consequently, the DAS 6E is configured to process the X-ray detection elements 9 in a group by the same circuit and the X-ray detection elements 9 belonging to adjacent groups by a different QV chip. As a result, the DAS 6E can distribute the signal processing characteristics of adjacent groups on the X-ray detection element array 7 in such a manner that the adjacent groups of X-ray detection elements 9 have non-identical, non-similar, widely different signal processing characteristics.

The QV amplifier unit 12E has QV chips as a plurality of IC chips and each QV chip has a plurality of QV amplifiers. FIG. 8 illustrates only a first QV chip having 16 QV amplifiers (QV 1 to QV 16) and a second QV chip having 16 QV amplifiers (QV 17 to QV 32). Each photodiode 11 of the X-ray detection elements 9 outputs an X-ray detection signal as an electrical signal. Each QV amplifier converts the electrical signal to a voltage signal and amplifies the voltage signal.

The AD converter unit 13E has AD chips as a plurality of IC chips, and each AD chip has a plurality of AD converters. FIG. 8 illustrates a first AD chip having four AD converters (ADC 1 to ADC 4), a second AD chip having four AD converters (ADC 5 to ADC 8), and so on. Each AD converter converts a voltage signal generated by a QV amplifier to a digital signal.

The first signal path 14E forms a signal path starting at each X-ray detection element 9 and reaching the QV amplifier unit 12E. The second signal path 15E forms a signal path starting at the QV amplifier unit 12E and reaching the AD converter unit 13E.

Specifically, as illustrated in FIG. 8, the DAS 6E is configured such that one QV chip is shared by the elements [1, 1] to [4, 1] in the first line, the elements [1, 5] to [4, 5] in the fifth line, the elements [1, 9] to [4, 9] in the ninth line, and the elements [1, 13] to [4, 13] in the thirteenth line. As illustrated in FIG. 8, the DAS 6E is configured such that one QV chip is shared by the elements [1, 2] to [4, 2], [1, 6] to [4, 6], [1, 10] to [4, 10], and [1, 14] to [4, 14].

As illustrated in FIG. 8, the DAS 6E is configured such that the elements [1, 1] to [4, 1] share one AD chip. In addition, the DAS 6E is configured such that the elements [1, 5] to [4, 5] share one AD chip.

Note that the DAS 6E is not limited to the configuration in which a group consists of four X-ray detection elements 9 continuing in the same line and in the channel direction. For example, a group may consist of four elements [1, 1] to [1, 4] in a different line and in the same channel or a group may consist of four elements [1, 1] to [2, 2] in a matrix form. Moreover, the number of X-ray detection elements 9 in a group is not limited to 4.

Hereinafter, an operation of the X-ray CT apparatus UE will be described.

According to the conventional DAS 6Y (illustrated in FIGS. 11 and 12), each X-ray detection signal generated by four X-ray detection elements 9Y continuing in the channel direction and in the same line is signal-processed by the same QV chip and the same AD chip. In other words, each X-ray detection signal generated by the elements [1, 1] to [4, 1] and the elements [1, 1] to [1, 4] is signal-processed under similar signal processing characteristics. Consequently, the DAS 6Y causes an uneven distribution of signal processing characteristics, and thus artifacts are likely to appear noticeably.

In contrast to this, according to the DAS 6E of the X-ray CT apparatus UE, each X-ray detection signal generated by a group of four elements [1, 1] to [4, 1] continuing in the channel direction and in the same line is signal-processed by the first QV chip. Each X-ray detection signal generated by another group of four elements [5, 1] to [8, 1] adjacent to the group is signal-processed by a QV chip different from the first QV chip. In addition, each X-ray detection signal generated by another group of four elements [1, 2] to [4, 2] adjacent to the group is signal-processed by a QV chip different from the first QV chip. That is, according to the DAS 6E, the X-ray detection signals generated within a group have similar signal processing characteristics, but the X-ray detection signals generated by adjacent groups have non-identical, non-similar, and widely different signal processing characteristics.

Hereinafter, advantages of the X-ray CT apparatus UE will be described.

The DAS 6E of the X-ray CT apparatus UE has a characteristic distribution connection structure in which adjacent groups of X-ray detection elements 9 have non-identical, non-similar, widely different signal processing characteristics. Consequently, the X-ray CT apparatus UE can reduce the uneven distribution of signal processing characteristics of the DAS 6E and can reduce artifacts caused by a variation of signal processing characteristics without equalizing the signal processing characteristics on the X-ray detection element array 7.

Seventh Embodiment

The schematic configuration view of an X-ray CT apparatus UF of a seventh embodiment is the same as FIG. 1 and the partially detailed view is the same as FIG. 2.

Figure 9:
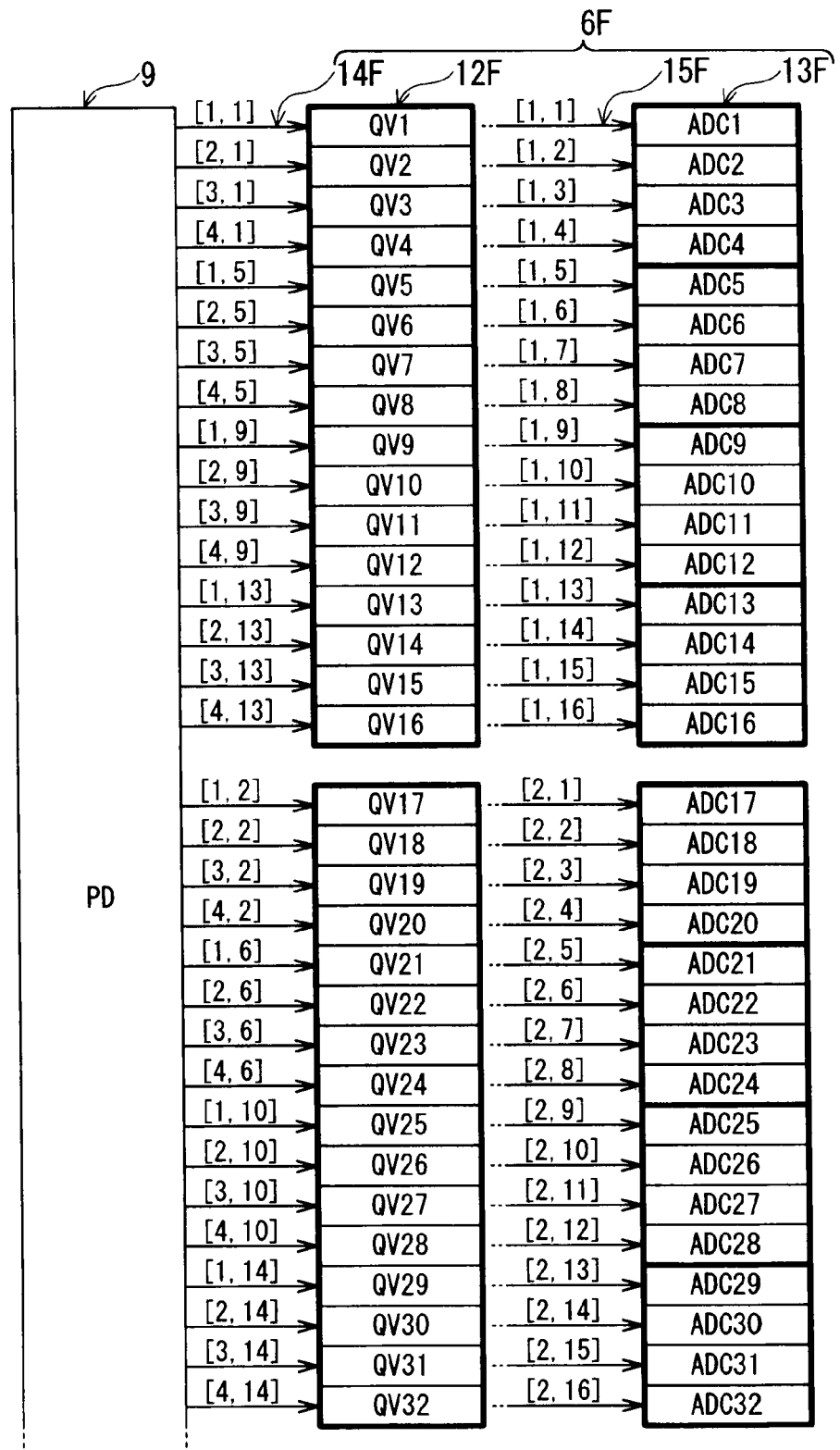
FIG. 9 is a diagram illustrating a configuration of a DAS according to the X-ray CT apparatus of the seventh embodiment.

FIG. 9 is a diagram illustrating a DAS 6F according to the X-ray CT apparatus UF of the seventh embodiment. The DAS 6F of the X-ray CT apparatus UF of the seventh embodiment is a modified example of the DAS 6E illustrated in FIG. 8. Note that in FIG. 9, the description is made by adding "F" to the end of the reference numeral or character of a component modifying or newly added to a corresponding component of FIG. 8.

According to the DAS 6E of the X-ray CT apparatus UE illustrated in FIG. 8, the adjacent elements [1, 1], [2, 1], [3, 1], and [4, 1] in the same group are signal-processed by the same QV chip and the same AD chip. In other words, the adjacent elements [1, 1], [2, 1], [3, 1], and [4, 1] in the same group have similar signal processing characteristics. However, the DAS 6F of the X-ray CT apparatus UF illustrated in FIG. 9 is configured such that even the adjacent elements [1, 1], [2, 1], [3, 1], and [4, 1] are recombined between a combination of X-ray detection elements 9 to be processed by one QV chip and a combination of X-ray detection elements 9 to be processed by one AD chip so that the signal processing characteristics do not become similar.

For example, according to the DAS 6F, the element [1, 1] is combined with the elements [2, 1], [3, 1], and [4, 1] in the QV chip, but is combined with the elements [1, 2], [1, 3], and [1, 4] in the AD chip.

Hereinafter, advantages of the X-ray CT apparatus UF will be described.

The DAS 6F of the X-ray CT apparatus OF has a characteristic distribution connection structure in which adjacent X-ray detection elements 9 have non-identical signal processing characteristics. Consequently, the X-ray CT apparatus UF can reduce the uneven distribution of signal processing characteristics of the DAS 6F and can reduce artifacts caused by a variation of signal processing characteristics without equalizing the signal processing characteristics on the X-ray detection element array 7. Moreover, in comparison with the DAS 6E of the X-ray CT apparatus UE of the sixth embodiment, the X-ray CT apparatus UF can well reduce the uneven distribution of signal processing characteristics of the DAS 6F, and thus artifacts are more difficult to appear noticeably.

Hereinbefore, the X-ray CT apparatuses U to UF of the present embodiments have been described based on the nine DASs 6 to 6F, but a specific configuration of the X-ray CT apparatus of the present invention is not limited to the embodiments. Design modifications and additions are allowed to be made to the X-ray CT apparatus of the present invention without departing from the spirit and scope of the invention claimed within the scope of the appended claims.

For example, the DASs 6 to 6F may be configured such that a combination of channels undergoing an AD conversion by each AD converter may be made different for each line or the DASs 6 to 6F may be configured such that a combination of the first signal path 14 shared by the second signal path 15 may be made different for each line.

Moreover, the characteristic distribution connection structure of the DASs 6 to 6F may be provided at an appropriate position such as the first signal path 14 starting at the X-ray detection element 9 and reaching the QV amplifier unit 12 and the second signal path 15 starting at the QV amplifier unit 12 and reaching the AD converter unit 13.

Further, the DASs 6 to 6F and X-ray CT apparatuses U to UF may be manufactured by recombining the connection between a signal path and an X-ray detection element 9 so that the signal path having the same or similar signal processing characteristics on the X-ray detection element array 7 has a higher dispersion than the signal path at or after completion of the DASs 6 to 6F.

What is claimed is:
1. An X-ray CT apparatus comprising:
an X-ray detector including a plurality of X-ray detection arrays, each X-ray detection array including a plurality of X-ray detection elements arranged in a matrix, the matrix having a plurality of columns of X-ray detection elements arranged in a channel direction, the channel direction being substantially orthogonal to a body axial direction, and a plurality of rows of X-ray detection elements arranged in a slice direction which is substantially parallel to the body axial direction;
an amplifier unit having a plurality of amplifiers;
a first connection unit connecting the plurality of X-ray detection elements and the amplifier unit;
an AD converter unit having a plurality of AD converters; and
a second connection unit connecting the amplifier unit and the AD converter unit,
wherein each of the plurality of amplifiers is connected to a different group of X-ray detection elements from among the plurality of X-ray detection elements within one of the plurality of X-ray detection arrays, and none of the X-ray elements within any of the groups of X-ray detection elements connected to a single amplifier is directly adjacent to another X-ray detection element within the same group in either the channel direction or the slice direction in the matrix of the X-ray detection array.

2. An X-ray CT apparatus comprising:
an X-ray detector including a plurality of X-ray detection arrays, each X-ray detection array including a plurality of X-ray detection elements arranged in a matrix, the matrix having a plurality of columns of X-ray detection elements arranged in a channel direction, the channel direction being substantially orthogonal to a body axial direction, and a plurality of rows of X-ray detection elements arranged in a slice direction which is substantially parallel to the body axial direction;
an amplifier unit which has a plurality of amplifier chips each including a plurality of amplifiers;
a first connection unit connecting the plurality of X-ray detection elements and the amplifier unit;
an AD converter unit having a plurality of AD converters; and
a second connection unit connecting the amplifier unit and the AD converter unit,
wherein each of the plurality of amplifiers is connected to a different group of X-ray detection elements from among the plurality of X-ray detection elements within one of the plurality of X-ray detection arrays, and none of the X-ray elements within any of the groups of X-ray detection elements connected to a single amplifier is directly adjacent to another X-ray detection element within the same group in a slice direction in the matrix of the X-ray detection array, and at least two X-ray detection elements that are adjacent to each other in the slice direction in the matrix of the X-ray detection array are connected to different amplifier chips.

3. An X-ray CT apparatus comprising:
an X-ray detector including a plurality of X-ray detection arrays, each X-ray detection array including a plurality of X-ray detection elements arranged in a matrix, the matrix having a plurality of columns of X-ray detection elements arranged in a channel direction, the channel direction being substantially orthogonal to a body axial direction, and a plurality of rows of X-ray detection elements arranged in a slice direction which is substantially parallel to the body axial direction;
an amplifier unit having a plurality of amplifiers;
a first connection unit connecting the plurality of X-ray detection elements and the amplifier unit;
an AD converter unit which has a plurality of AD chips each including a plurality of AD converters; and
a second connection unit connecting the amplifier unit and the AD converter unit,
wherein each of the plurality of AD chips is connected to a different group of X-ray detection elements from among the plurality of X-ray detection elements within one of the X-ray detection arrays, and none of the X-ray detection elements within any of the groups of X-ray detection elements connected to a single AD chip is directly adjacent to another X-ray detection element within the same group in the slice direction in the matrix of the X-ray detection array.

4. The X-ray CT apparatus according to claim 3,
wherein the amplifier unit has a plurality of amplifier chips each including a plurality of amplifiers, and
at least two X-ray detection elements that are adjacent to each other in the slice direction in the matrix of the X-ray detection array are connected to different amplifier chips.

5. An X-ray CT apparatus comprising:
an X-ray detector including a plurality of X-ray detection arrays, each X-ray detection array including a plurality of X-ray detection elements arranged in a matrix, the matrix having a plurality of columns of X-ray detection elements arranged in a channel direction, the channel direction being substantially orthogonal to a body axial direction, and a plurality of rows of X-ray detection elements arranged in a slice direction which is substantially parallel to the body axial direction;
an amplifier unit having a plurality of amplifiers;
a first connection unit connecting the plurality of X-ray detection elements and the amplifier unit;
an AD converter unit having a plurality of AD converters; and
a second connection unit connecting the amplifier unit and the AD converter unit,
wherein each of the plurality of AD converters is connected to a different group of X-ray detection elements from among the plurality of X-ray detection elements within one of the X-ray detection arrays, and none of the X-ray elements within any of the groups of X-ray detection elements connected to a single AD converter is directly adjacent to another X-ray detection element within the same group in either the channel direction or the slice direction in the X-ray detector matrix of the X-ray detection array.

* * * * *